(12) United States Patent
Barrett et al.

(10) Patent No.: US 9,173,988 B2
(45) Date of Patent: Nov. 3, 2015

(54) SENSOR CLIP ASSEMBLY FOR AN OPTICAL MONITORING SYSTEM

(75) Inventors: Louis L. Barrett, West Point, UT (US); David W. Peterson, Clinton, UT (US); N. Diane Hudkins, Hooper, UT (US); Matthew A. Stowell, South Ogden, UT (US); Kristian A. Sammann, Murray, UT (US); Bemjamin D. Jensen, Logan, UT (US); Douglas L. Cox, Morgan, UT (US); Perry N. Law, Centerville, UT (US); Ronald S. Glaittli, Bountiful, UT (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 951 days.

(21) Appl. No.: 13/030,212

(22) Filed: Feb. 18, 2011

(65) Prior Publication Data

US 2012/0120384 A1  May 17, 2012

Related U.S. Application Data (60) Provisional application No. 61/414,654, filed on Nov. 17, 2010.

(51) Int. Cl.
*A61B 5/1455* (2006.01)
*A61M 1/36* (2006.01)
*A61B 5/145* (2006.01)
*A61B 5/00* (2006.01)

(52) U.S. Cl.
CPC .............. *A61M 1/367* (2013.01); *A61B 5/1455* (2013.01); *A61B 5/14535* (2013.01); *A61B 5/6866* (2013.01); *A61M 1/36* (2013.01); *A61M 1/3609* (2014.02); *A61M 2205/3306* (2013.01); *A61M 2205/3313* (2013.01); *A61M 2230/207* (2013.01)

(58) Field of Classification Search
CPC ............. A61B 5/1455; A61B 5/14535; A61B 5/6866; A61M 1/3609; A61M 2205/3306; A61M 2230/207
USPC .................................. 600/310, 322, 323, 344
See application file for complete search history.

(56) References Cited

U.S. PATENT DOCUMENTS

| | | |
|---|---|---|
| 2,357,238 A | 8/1944 | Trimble |
| D206,714 S | 1/1967 | Badkar |
| D212,218 S | 9/1968 | Norton |
| 3,507,951 A | 4/1970 | Baily |
| 3,580,683 A | 5/1971 | Schulkind |

(Continued)

FOREIGN PATENT DOCUMENTS

| | | |
|---|---|---|
| CN | 101015455 A | 8/2007 |
| CN | 101113477 A | 1/2008 |

(Continued)

OTHER PUBLICATIONS

International Search Report PCT/US2011/061273 (Mar. 13, 2012).

(Continued)

*Primary Examiner* — Eric Winakur
(74) *Attorney, Agent, or Firm* — Leydig, Voit & Mayer, Ltd.

(57) ABSTRACT

A sensor clip assembly for an optical blood monitoring system includes a circuit board with a microprocessor that is programmed with a ratiometric model to calculate hematocrit and/or oxygen saturation levels of a patient.

18 Claims, 7 Drawing Sheets

(56) References Cited

U.S. PATENT DOCUMENTS

| | | | |
|---|---|---|---|
| 3,728,032 A | 4/1973 | Noll | |
| 3,740,156 A | 6/1973 | Heigl et al. | |
| 4,243,883 A | 1/1981 | Schwarzmann | |
| D270,281 S | 8/1983 | Andersen et al. | |
| 4,444,498 A | 4/1984 | Heinemann | |
| 4,784,768 A | 11/1988 | Mathieu | |
| 4,936,993 A | 6/1990 | Nomura | |
| 5,073,171 A | 12/1991 | Eaton | |
| 5,171,456 A | 12/1992 | Hwang et al. | |
| D335,096 S | 4/1993 | Marsh | |
| 5,222,948 A | 6/1993 | Austin et al. | |
| 5,231,464 A | 7/1993 | Ichimura et al. | |
| 5,247,434 A | 9/1993 | Peterson et al. | |
| 5,312,535 A | 5/1994 | Waska et al. | |
| 5,351,686 A | 10/1994 | Steuer et al. | |
| 5,366,630 A | 11/1994 | Chevallet | |
| 5,372,136 A | 12/1994 | Steuer et al. | |
| 5,456,253 A | 10/1995 | Steuer et al. | |
| 5,458,566 A | 10/1995 | Herrig et al. | |
| 5,476,764 A | 12/1995 | Bitensky | |
| 5,670,050 A | 9/1997 | Brose et al. | |
| 5,674,390 A | 10/1997 | Matthews et al. | |
| 5,676,644 A | 10/1997 | Toavs et al. | |
| 5,729,333 A | 3/1998 | Osten et al. | |
| 5,730,712 A | 3/1998 | Falkvall et al. | |
| 5,762,805 A | 6/1998 | Truitt et al. | |
| 5,769,815 A | 6/1998 | Utterberg | |
| 5,779,529 A | 7/1998 | Bizer | |
| 5,792,052 A | 8/1998 | Isaacson et al. | |
| D409,750 S | 5/1999 | Hacker | |
| 6,018,673 A | 1/2000 | Chin et al. | |
| 6,069,687 A | 5/2000 | Briggs | |
| 6,090,061 A | 7/2000 | Steuer et al. | |
| 6,284,131 B1 | 9/2001 | Hogard et al. | |
| 6,284,142 B1 | 9/2001 | Muller | |
| 6,510,330 B1 | 1/2003 | Enejder | |
| 6,554,788 B1 | 4/2003 | Hunley et al. | |
| 6,746,415 B1 | 6/2004 | Steuer et al. | |
| 6,784,820 B1 | 8/2004 | Casalegno et al. | |
| 7,018,353 B2 | 3/2006 | Hunley et al. | |
| D518,573 S | 4/2006 | French | |
| 7,241,825 B2 | 7/2007 | Koga et al. | |
| 7,247,143 B2 | 7/2007 | Law et al. | |
| 7,671,974 B2 | 3/2010 | O'Mahony et al. | |
| D623,302 S | 9/2010 | Barrett et al. | |
| D625,824 S | 10/2010 | Brackett et al. | |
| D630,536 S | 1/2011 | Pettit | |
| D654,999 S | 2/2012 | Barrett et al. | |
| 8,133,194 B2 | 3/2012 | Szamosfalvi et al. | |
| 8,287,739 B2 | 10/2012 | Barrett et al. | |
| 8,315,682 B2 * | 11/2012 | Such et al. | 600/323 |
| 8,328,748 B2 | 12/2012 | Law et al. | |
| 8,333,724 B2 | 12/2012 | Barrett et al. | |
| D684,695 S | 6/2013 | Green et al. | |
| D684,697 S | 6/2013 | Green et al. | |
| 8,517,968 B2 | 8/2013 | Barrett et al. | |
| D698,440 S | 1/2014 | Lombardi et al. | |
| 9,002,655 B2 | 4/2015 | Bene | |
| 2001/0016699 A1 | 8/2001 | Burbank et al. | |
| 2001/0021817 A1 | 9/2001 | Brugger et al. | |
| 2001/0037079 A1 | 11/2001 | Burbank et al. | |
| 2001/0041892 A1 | 11/2001 | Burbank et al. | |
| 2002/0103453 A1 | 8/2002 | Burbank et al. | |
| 2002/0147423 A1 | 10/2002 | Burbank et al. | |
| 2003/0009123 A1 | 1/2003 | Brugger et al. | |
| 2003/0045784 A1 | 3/2003 | Palatnik et al. | |
| 2003/0070969 A1 | 4/2003 | Muller et al. | |
| 2003/0097087 A1 | 5/2003 | Gura | |
| 2003/0143116 A1 | 7/2003 | Zheng et al. | |
| 2003/0196949 A1 | 10/2003 | Sunohara et al. | |
| 2003/0210390 A1 | 11/2003 | O'Mahony et al. | |
| 2003/0212316 A1 | 11/2003 | Leiden et al. | |
| 2004/0087845 A1 * | 5/2004 | Katarow et al. | 600/323 |
| 2005/0094127 A1 | 5/2005 | O'Mahony et al. | |
| 2006/0036185 A1 | 2/2006 | Lewicke et al. | |
| 2006/0144776 A1 | 7/2006 | Mishkin et al. | |
| 2006/0226079 A1 | 10/2006 | Mori et al. | |
| 2006/0290625 A1 | 12/2006 | Sugimoto | |
| 2007/0015963 A1 | 1/2007 | Fengler et al. | |
| 2007/0100219 A1 | 5/2007 | Sweitzer et al. | |
| 2007/0149871 A1 | 6/2007 | Sarussi et al. | |
| 2007/0179433 A1 | 8/2007 | Jonsson et al. | |
| 2008/0081970 A1 | 4/2008 | Boyce et al. | |
| 2008/0129047 A1 | 6/2008 | Blivet et al. | |
| 2008/0300570 A1 | 12/2008 | Fowles et al. | |
| 2009/0054751 A1 * | 2/2009 | Babashan et al. | 600/324 |
| 2009/0247850 A1 | 10/2009 | Porges | |
| 2010/0004518 A1 | 1/2010 | Vo et al. | |
| 2010/0110416 A1 | 5/2010 | Barrett et al. | |
| 2010/0113891 A1 | 5/2010 | Barrett et al. | |
| 2010/0168531 A1 | 7/2010 | Shaltis et al. | |
| 2011/0004082 A1 | 1/2011 | Poeze et al. | |
| 2011/0022077 A1 | 1/2011 | Green et al. | |
| 2011/0160679 A1 | 6/2011 | Okiyama et al. | |
| 2012/0120384 A1 | 5/2012 | Barrett et al. | |
| 2012/0154789 A1 | 6/2012 | Barrett et al. | |

FOREIGN PATENT DOCUMENTS

| | | |
|---|---|---|
| EP | 0 274 178 A1 | 7/1988 |
| EP | 467805 A1 | 1/1992 |
| EP | 0 990 444 A2 | 4/2000 |
| GB | 1 583 023 A | 1/1981 |
| JP | 56031085 A | 3/1981 |
| JP | 09-229847 | 9/1997 |
| JP | 2005-501589 A | 1/2005 |
| JP | 2006199845 A | 8/2006 |
| JP | 2009-125316 A | 6/2009 |
| JP | 2009-216711 | 9/2009 |
| WO | WO 93/06456 A1 | 4/1993 |
| WO | WO 93/06774 A1 | 4/1993 |
| WO | WO 94/27495 A1 | 12/1994 |
| WO | WO 98/37801 A1 | 9/1998 |
| WO | WO 00/33053 A1 | 6/2000 |
| WO | WO 01/87151 A2 | 11/2001 |
| WO | WO 01/93944 A1 | 12/2001 |
| WO | WO 02/078783 A2 | 10/2002 |

OTHER PUBLICATIONS

Office action for co-pending Canadian Patent Application No. 2,742,619, dated Aug. 5, 2013.
Original claims as filed for co-pending Canadian Patent Application No. 2,742,619 including a Voluntary Amendment dated Sep. 6, 2011.
Office action for co-pending Canadian Patent Application No. 2,742,794, including original claims as filed, date unknown.
Official action for co-pending European Patent Application No. 11 755 533.4 dated Apr. 16, 2013.
Official action for co-pending European Patent Application No. 11 754 974.1 dated Apr. 16, 2013.
Blood Chamber 2001—Admitted Prior Art.
CL Photo 2000—Admitted Prior Art.
Blood Chamber Instruction Sheet 2001—Admitted Prior Art.
International Search Report and Written Opinion for related International No. PCT/US2012/026637 dated Jun. 6, 2012.
Sacker-Berstein, Jonathan D., M.D., et al., "How Should Diuretic-Refractory Colume-OVerloaded Heart Failure Patients Be Managed?", *The Journal of Invasive Cardiology*, vol. 15., No. 10 (Oct. 2003), pp. 585-590, retrieved from http;//www.medscape.com/viewarticle/463509_print on Mar. 11, 2013, pp. 1-11.
Jaski, Brian E., M.D., "Peripherally Inserted Veno-Venous Ultrafiltration for Rapid Treatment of Volume Overloaded Patients", *Journal of Cardiac Failure*, vol. 9, No. 3 (Jun. 2003) pp. 227-231.
Steuer, et al., "Optical Measurement of Hematocrit and Other Biological Constituents in Renal Therapy", *Advances in Renal Replacement Therapy*, vol. 6, No. 3 (Jul. 1999), pp. 217-224).
Gardner, "Exponential Smoothing: The State of Art", *Journal of Forecasting*, vol. 4, 1985, (pp. 1-28).
Baum, "An Introduction to Modern Econometrics Using Strata", *StaraCorp., LP*, 2006, Chapter 9, (pp. 2165-2245).

(56) References Cited

OTHER PUBLICATIONS

International Search Report and Written Opinion for International No. PCT/US2009/057964, dated Jun. 18, 2010.
Logman, Dirren H., MHGM, et al., "Altitude Correction fro Hemoglobin", *European Journal of Clinical Nutrition*, (Believed to be no longer in publication).
Peer Review, "Effects of CPD and K2EDTA Preservatives on Blood Sample Hematocrit", *Asaio Abstract Submission Information, 45th Annual Conference*, San Diego, Jun. 3-5, 1999.
Cohen, Jennifer H., et al., "Hemoglobin Correction Factors for Estimating the Prevalence of Iron Deficiency Anemia in Pregnant Women Residing at High Altitudes in Bolivia", retrieved from http://www.scielo.php?script=sci_arttext&pid=S1020-49891999001100004 on Jun. 19, 2009 (12 pages).
Zhang, S., Ph.D., et al., Hematocrit Measurement Error Due to Time Dependence of Hematocrit fro EDTA-Preserved Blood Samples, *ANA 36 Annual Meeting & Scientific Exposition*, http//www.call4abstracts.com/ams/main/finalpreview, site visited Jun. 25, 2003.
Crit-Line Hematrocrt Accuracy Hema Metrics, vol. 1, *Tech Note No. 11* (Rev D), pp. 1-4, Feb. 24, 2003.
*ScienceStockroom Flow Through Cuvette*, p. 8/14.
Barrett, Lee, "Effects of CPD and $K_3$ EDTA Preservatives on Blood Sample Hematocrit", Abstract Submission, *ASAIO, 45th Annual Conference*, San Diego (Jun. 1999).
First Office action from foreign co-pending Chinese Patent Application No. 201180042991.4 dated May 21, 2014.
Official Action for European Patent Application No. 11 801 888.6 dated Jun. 5, 2014.
Office action for Australian Patent Application No. 2011299393 dated Jun. 27, 2013.
Official Action for European Patent Application No. 11 801 888.6 dated Apr. 25, 2014.
Written Opinion for International Patent Application No. PCT/US2011/061273.
Japanese Office action for Japanese Patent Application No. 58245/2013, dated Dec. 24, 2014, (5 pages).
Chinese Office action for Chinese Patent Application No. 201180042991.4, dated Jan. 19, 2015, (9 pages).
Official action from co-pending Canadian Patent Application No. 2,742,619, dated Nov. 6, 2014 (5 pages).
Examination Report for Australian Application No. 2011329788, dated Jun. 17, 2015.
Office action from Chinese Patent Application No. 201180055375.2, dated Mar. 16, 2015, (43 pages total).
Official Action for European Patent Application No. 11801888.6, dated Apr. 9, 2015.
Official Action for Chinese Patent Application No. 201280010099.2, dated Apr. 22, 2015.
Examination Report dated Aug. 5, 2015 for related Australian Application No. 2012222113.
Third Office action dated Jul. 31, 2015 for related Chinese Paten Application No. 201180042991.4.
Japanese Examination Report dated Aug. 18, 2015 for related Japanese application No. 2013-540034.
Mexican Office action dated Aug. 20, 2015 for related Mexican Application No. MX/a/2013/009761.

\* cited by examiner

SENSOR CLIP ASSEMBLY FOR AN OPTICAL MONITORING SYSTEM

CROSS REFERENCE TO RELATED APPLICATION

This application claims priority from Provisional U.S. Patent Application No. 61/414,654, filed Nov. 17, 2010.

FIELD OF THE INVENTION

The invention relates to optical monitoring systems, and more specifically systems for monitoring the presence or concentration of constituents in blood. The invention is particularly useful for the real-time measurement of hematocrit and/or oxygen saturation levels when monitoring a patient during hemodialysis or other procedure involving extracorporeal blood flow.

BACKGROUND

Patients with kidney failure or partial kidney failure typically undergo hemodialysis treatment in order to remove toxins and excess fluids from their blood. To do this, blood is taken from a patient through an intake needle or catheter that draws blood from a blood vessel located in a specifically accepted access location (for example, a shunt surgically placed in an arm, thigh, subclavian, etc.). The needle or catheter is connected to extracorporeal tubing that is fed to a peristaltic pump and then to a dialyzer which cleans the blood and removes excess water. The cleaned blood is then returned to the patient through additional extracorporeal tubing and another needle or catheter. Sometimes, a heparin drip is located in the hemodialysis loop to prevent the blood from coagulating particularly in the dialysis filter. By way of background, as the drawn blood passes through the dialyzer, it travels in straw-like tubes within the dialyzer that serve as semi-permeable passageways for the unclean blood. Fresh dialysate solution enters the dialyzer at its downstream end. The dialysate surrounds the straw-like tubes and flows through the dialyzer in the opposite direction of the blood flowing through the tubes. Fresh dialysate collects toxins passing through the straw-like tubes by diffusion and excess fluids in the blood by ultra filtration.

It is known in the art to use an optical blood monitoring system during hemodialysis, such as the CRIT-LINE® monitoring system which is sold by the assignee of this application. The CRIT-LINE® blood monitoring system uses optical techniques to non-invasively measure in real-time the hematocrit and oxygen saturation levels of blood flowing through a hemodialysis system. In the CRIT-LINE® system, a sterile, single-use blood chamber is attached in-line to the extracorporeal tubing normally on the arterial side of the dialyzer. The blood chamber provides a viewing point for optical sensors during the hemodialysis procedure. As described in more detail below under the heading Detailed Description of the Drawings, the blood chamber used in the current system comprises a molded body made of clear medical grade polycarbonate. The chamber body along with the tube set and dialyzer filter are replaced for each respective patient. The blood lines and blood chamber are replaced for each treatment though the personal filter for each patient is often cleaned and reused over several treatments. The blood chamber provides an internal blood flow cavity, a flat viewing region and two viewing lenses: one being integrally molded with the body of the polycarbonate blood chamber and the other being welded into place. The LED photo emitters and the photodetectors for the optical blood monitor are contained on a sensor clip assembly that is clipped into place on the blood chamber over the lenses. Multiple wavelengths of visible and infrared light are directed through the blood chamber and the patient's blood flowing therethrough, and the resulting intensity of each wavelength are detected. The preferred wavelengths to monitor hematocrit are: a) about 810 nm (e.g. 829 nm), which is substantially isobestic for red blood cells, and b) about 1300 nm, which is substantially isobestic for water. The preferred wavelengths to monitor oxygen saturation are: a) about 660 nm, and b) about 810 (e.g., 829 nm). The system includes a sensor clip assembly having an LED emitter for each wavelength (e.g. 660 nm, 810 nm, and 1300 nm) and also a silicon photodetector to detect the intensity of the 660 nm and 810 nm light and an indium gallium arsenide photodetector to detect the intensity of the 1300 nm light. Signals from the photodetectors representing the intensity of each wavelength (660 nm, 810 nm and 1300 nm) are transmitted from the sensor clip assembly to a stand-alone electronic controller.

A ratiometric technique implemented in the CRIT-LINE® controller, substantially as disclosed in U.S. Pat. No. 5,372,136 entitled "System and Method for Non-Invasive Hematocrit Monitoring", issued on Dec. 13, 1999 and assigned to the assignee of the present application, uses the information transmitted from the sensor clip assembly to calculate the patient's hematocrit and oxygen saturation levels in real-time. The hematocrit value, as is widely known in the art, is the percentage determined by dividing the volume of the red blood cells in a given whole blood sample by the overall volume of the blood sample. In a clinical setting, the actual percentage change in blood volume occurring during hemodialysis can be determined, in real-time, from the change in the measured hematocrit. Thus, an optical blood monitor, such as the CRIT-LINE® monitor, is able to non-invasively monitor not only the patient's hematocrit level but also the change in the patient's blood volume in real-time during a hemodialysis treatment session. The ability to monitor real-time change in blood volume facilitates safe, effective hemodialysis and the ability to manage body fluid retention.

The mathematical ratiometric model for determining the hematocrit value can be represented by the following equation:

$$HCT = f\left[\frac{\ln\left(\frac{i_{810}}{I_{0-810}}\right)}{\ln\left(\frac{i_{1300}}{I_{0-1300}}\right)}\right] \quad \text{Eq. (1)}$$

where $i_{810}$ is the infrared light intensity detected by a photodetector at 810 nm, $i_{1300}$ is the infrared light intensity detected at 1300 nm and $I_{0-810}$ and $I_{0-1300}$ are constants representing the intensity incident on the blood accounting for losses through the blood chamber. The function $f[\ ]$ is a mathematical function which has been determined based on experimental data to yield the hematocrit value. Preferably, the function $f[\ ]$ in the above Eq. (1) is a relatively simply polynomial, e.g. a second polynomial. However, under some conditions, more complex fits such as a spline fit must be used.

The oxygen saturation level, or the oxygenated hemoglobin level, is determined using a ratiometric equation for red visible light at 660 nm and infrared light at 810 nm. The form of the preferred ratiometric model for determining oxygen saturation level is as follows:

$$SAT = g\left[\frac{\ln\left(\frac{i_{660}}{I_{0-660}}\right)}{\ln\left(\frac{i_{810}}{I_{0-810}}\right)}\right] \quad \text{Eq. (2)}$$

where $i_{660}$ is the light intensity of a photo receiver at 660 nm, $i_{810}$ is the infrared intensity detected at 810 nm and $I_{0-660}$ and $I_{0-810}$ are constants representing the intensity incident on the blood accounting for losses through the blood chamber. The function g[ ] is a mathematical function determined based on experimental data to yield the oxygen saturation level, again preferably a second order polynomial, although it may be useful to use a pair of second order polynomials or spline fitting techniques depending on the hematocrit value.

In the prior art CRIT-LINE® system, the stand alone controller includes a display that provides real-time blood monitoring data for the patient undergoing hemodialysis. The controller contains a microprocessor that calculates the displayed data calculated by the ratiometric models discussed above. The stand alone electronic controller also controls the operation of the respective LED emitters and the detectors in order to multiplex the independent wavelength measurements. The stand-alone controller also contains signal processing and noise reduction hardware and software, as well as calibration software. Preferably, calibration is accomplished in the field by placing the sensor clip assembly onto a verification filter (made of layered plastic having known optical qualities) that is mounted to either the sensor cable or the casing of the controller. Calibration software within the controller verifies the calibration of the unit, or allows the user to field calibrate the unit to bring it back to factory calibration settings. In some instances, it may be necessary to return the unit to the factory for calibration.

Normally, as mentioned, the controller is provided as a stand alone unit. In some applications, however, it is desired to integrate the capabilities of the CRIT-LINE® into OEM hemodialysis equipment or the like. In these applications, one or more custom designed circuit boards containing the ratiometric models, the sensor control software, the signal processing hardware and software and the calibration software are placed in the OEM equipment to receive the signals from the sensor clip assembly.

SUMMARY OF THE INVENTION

A primary objective of the invention is to eliminate the need for a stand-alone controller or custom designed circuit board and yet provide the functional capabilities of the CRIT-LINE® optical blood monitor. The preferred embodiment of the invention achieves this and other objectives by locating necessary hardware and software on a sensor clip assembly and transmitting serially formatted data signals (e.g. USB) from the sensor clip assembly.

A sensor clip assembly constructed in accordance with invention includes an emitter arm containing at least two LED emitters, and a detector arm containing at least one photodetector. Preferably, the emitter arm includes three LED emitters, one emitting visible or infrared light that is isobestic for red blood cells (e.g. about 810 nm), one that is isobestic for water (e.g. about 1300 nm), and one that is sensitive to oxygenated hemoglobin (e.g. about 660 nm). The detector arm preferably includes one or more silicon diode photodetector for detecting visible or infrared light at 660 nm and 810 nm, and an indium gallium arsenide diode photodetector for detecting infrared light at about 1300 nm. In accordance with the invention, a circuit board with a microprocessor is located on the sensor clip assembly. The microprocessor is programmed with at least one ratiometric model to calculate the concentration and/or presence of at least one constituent of interest in the blood from the detected visible or infrared light signals. The sensor clip assembly outputs a signal reflecting the calculated concentration or presence of the blood constituent of interest. Preferably, the signal output from the sensor clip assembly is a balanced digital data signal transmitted over a standard USB cable to enable common mode rejection. The USB cable can be connected to any equipment having USB driving capability.

The microprocessor on the sensor clip assembly is preferably programmed with a ratiometric model for determining the real-time hematocrit (HCT) for the patient based on the detected intensities for infrared light at the 810 nm and 1300 nm wavelengths. It also preferably includes a ratiometric model to calculate the real-time oxygen saturation level of the patient (SAT) from the detected intensity of the visible red light at 660 nm and the infrared light at 810 nm. The ratiometric technique is substantially disclosed the above mentioned U.S. Pat. No. 5,372,136 entitled "System and Method for Non-invasive Hematocrit Monitoring", which is hereby incorporated herein by reference.

The preferred sensor clip assembly includes an inner housing frame as well as a housing shell for the emitter arm and a housing shell for the detector arm, which results in a compartment within the emitter housing and another compartment within the detector housing. The inner housing frame includes a bridge having an internal channel that spans between the compartment in the emitter housing and the compartment in the detector housing. The bridge physically connects the emitter arm and the detector arm similar to the prior art clip assemblies. The sensor clip assembly is spring biased to bias the distal end of the emitter arm and the detector arm towards one another also similar to the prior art clip assemblies. The emitter LEDs are located in the distal end of the emitter arm and the detector diodes are located in the distal end of the detector arm. In accordance with the preferred embodiment of the invention, a receiver and communications board is located in the compartment in the detector housing. Also preferably, a power supply board is located in the same compartment. The receiver and communications circuit board receives analog signals from the photodetector diodes, which typically are small current (µAmpere) signals with a relatively large amount of background noise. The receiver and communications board converts the current signals (µA) into voltage (mV) signals, and also filters the signals to remove noise to an acceptable level. The clean voltage signals are then transmitted to the microprocessor. A processor circuit board including the microprocessor is located in the compartment in the emitter arm. As mentioned, the bridge between the emitter arm and the detector arm includes a channel. Ribbon cables passing through the channel electrically and physically connect the receiver and the communications board in the compartment in the detector housing to the processor circuit board in the compartment in the emitter housing. The preferred microprocessor includes a built-in A-D converter, and as mentioned is programmed with the ratiometric models to calculate the HCT and SAT of the patient. The microprocessor outputs digital signals representing HCT and SAT in real time over the ribbon cable to a USB communications chip or other serial interface chip located on the receiver and communications board in the detector housing. The microprocessor is preferably not only programmed with the ratiometric models but also programmed to control the operation of the LED emitters, and timing of the detection system. The power supply circuit board is affixed to the receiver and communications circuit board and also located within the detector housing. A USB or other serial data cable is connected to both the receiver and communications circuit board and the power supply board. For example, the USB data signals can be used by any equipment having USB driving capabilities. The signals can be received by a display and user interface unit, or can be received by OEM equipment.

As mentioned, a primary advantage of the invention is that the technology for optically monitoring the patient's hematocrit or oxygen saturation level can now be easily integrated into other electronic or medical equipment without requiring custom designed circuit boards to be integrated into the respective host devices. Implementing the data acquisition process and the mathematical conversion of the detected signals into serial (e.g. USB) data signals on circuit boards located on the sensor clip assembly provides several additional advantages, as well. First, it is advantageous to collect and convert the extremely small current (μA) signals from the silicon detector diode(s) and the indium gallium arsenide diode(s) without allowing the signals to be transmitted over a relatively long distance through wires, which introduce additional noise to the signal. Rather, the small signals are processed at the receiving point and the resulting measurements are quantified by a microprocessor and then transmitted by high level digital signaling to the host which is highly immune to cable noise. Further, a balanced data signal (e.g. USB) maintains the integrity of the transmitted data even better. Another advantage of the invention is that processing current signals (μA) from the detector diode(s) at the receiving point enables the system to drive the LED emitters with lower electrical currents. The use of lower LED drive currents not only reduces heat generation but also tends to extend the useful calibrated life of the LEDs.

Another advantage is that a sensor clip assembly made in accordance with the invention can be constructed to be a semi-durable device. Once the sensor clip falls out of calibration and can no longer be field calibrated, it will often be practical to simply replace the sensor clip assembly rather than return the sensor clip to the manufacturer for recalibration. The clinic can therefore continue operations without having to return systems or custom circuit boards to the manufacture for calibration.

Other features and advantages may be apparent to those skilled in the art upon review of the following drawings and description thereof.

BRIEF DESCRIPTION OF THE DRAWINGS

Prior Art

Preferred Embodiment of the Invention

DETAILED DESCRIPTION

Prior Art

Figure 1:
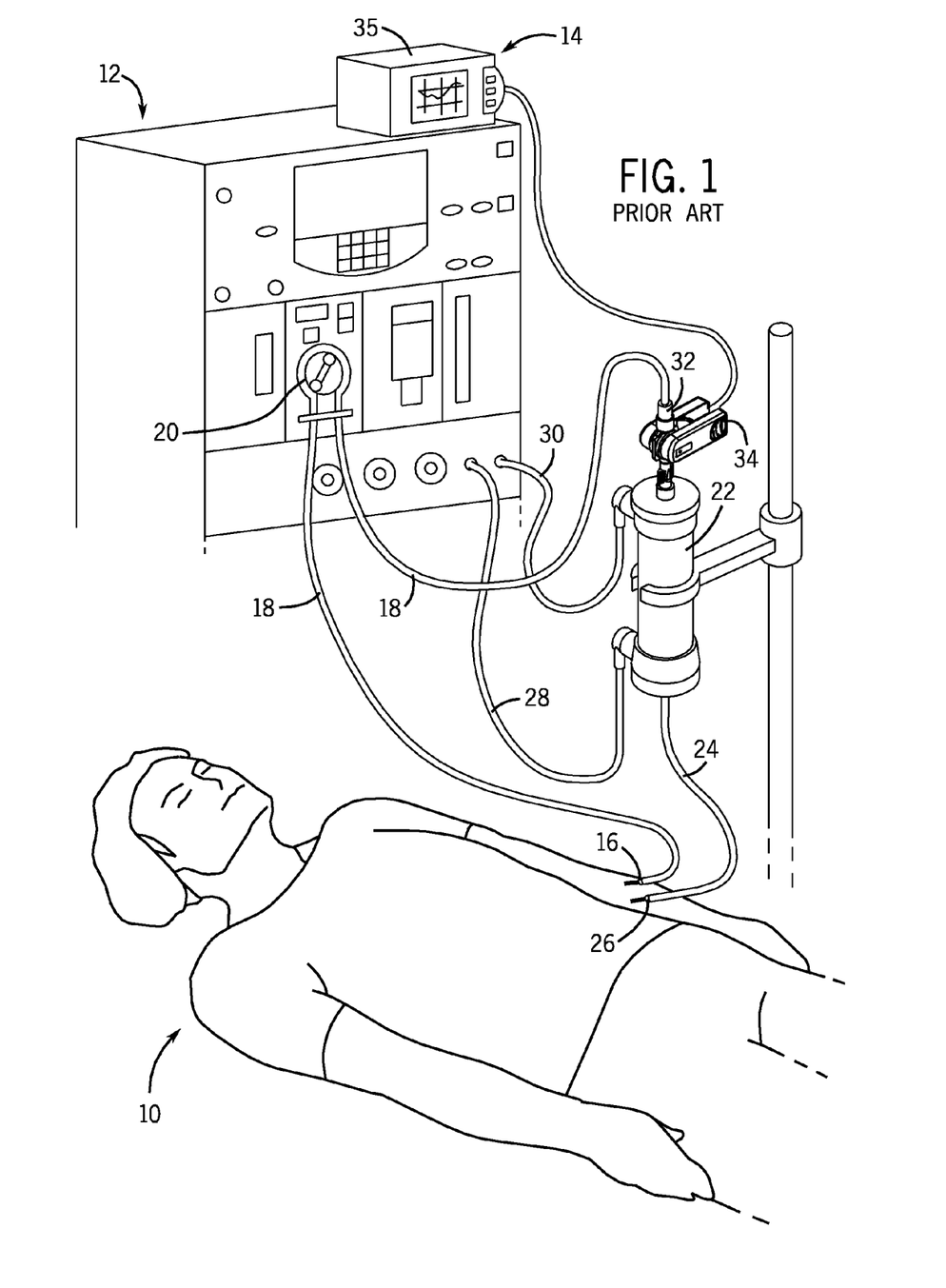
FIG. 1 is a perspective view of a patient undergoing hemodialysis treatment with a non-invasive, optical blood monitor that is monitoring the patient's blood in real-time as it passes through extracorporeal tubing in the hemodialysis system.

FIG. 1 illustrates a patient 10 undergoing hemodialysis treatment with a conventional hemodialysis system 12, and also illustrates a non-invasive, optical blood monitor 14 (i.e., a CRIT-LINE® optical blood monitoring system sold by the assignee). A typical hemodialysis clinic will have several hemodialysis systems 12 for treating patients.

An input needle or catheter 16 is inserted into an access site of the patient 10, such as shunt in the arm, and is connected to extracorporeal tubing 18 that leads to a peristaltic pump 20 and then to a dialyzer or blood filter 22. The dialyzer 22 removes toxins and excess fluid from the patient's blood. The dialysized blood is returned from the dialyzer 22 to the patient through extracorporeal tubing 24 and a return needle or catheter 26. The extracorporeal blood flow may receive a heparin drip to prevent clotting although that is not shown in FIG. 1. Excess fluids and toxins are removed by clean dialysate liquid which is supplied to the dialyzer 22 via tube 28 and removed for disposal via tube 30. A typical hemodialysis treatment session in the United States takes about 3 to 5 hours.

The optical blood monitor 14 includes a blood chamber 32, a sensor clip assembly 34, and a controller 35. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes LED photo emitters that emit infrared light at substantially 810 nm (e.g., 829 nm) which is isobestic for red blood cells and substantially 1300 nm, which is isobestic for water; and visible red light at substantially 660 nm, which is sensitive for oxygenated hemoglobin. The blood chamber 32 includes lenses so that the LED emitters and detector(s) can view the blood flowing through the blood chamber 32, and determine the patient's real-time hematocrit value and oxygen saturation value using ratiometric techniques generally known in the prior art.

Figure 2:
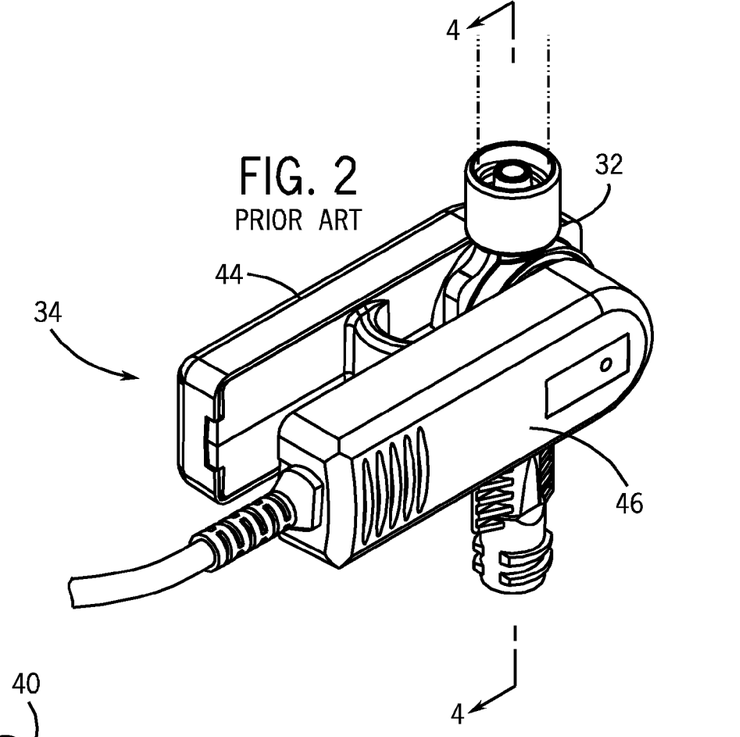
FIG. 2 is a perspective view showing a sensor clip assembly for the optical blood monitor shown in FIG. 1, the sensor clip assembly being positioned to sense blood flowing through a blood chamber connected in extracorporeal tubing of the hemodialysis system.
Figure 3:
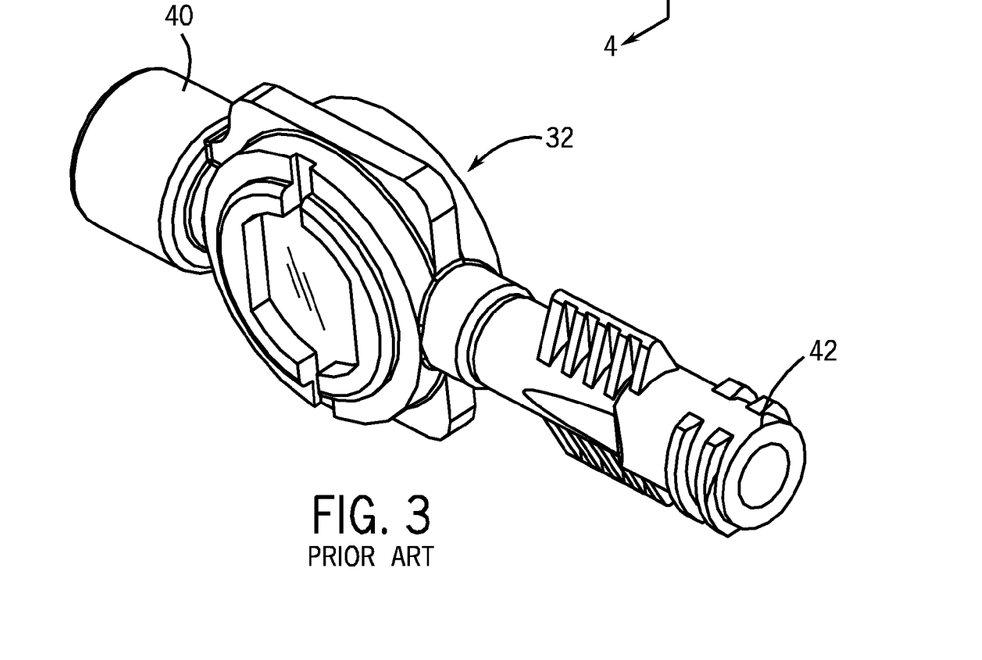
FIG. 3 is a detailed view of a prior art blood chamber shown in FIG. 2.
Figure 4:
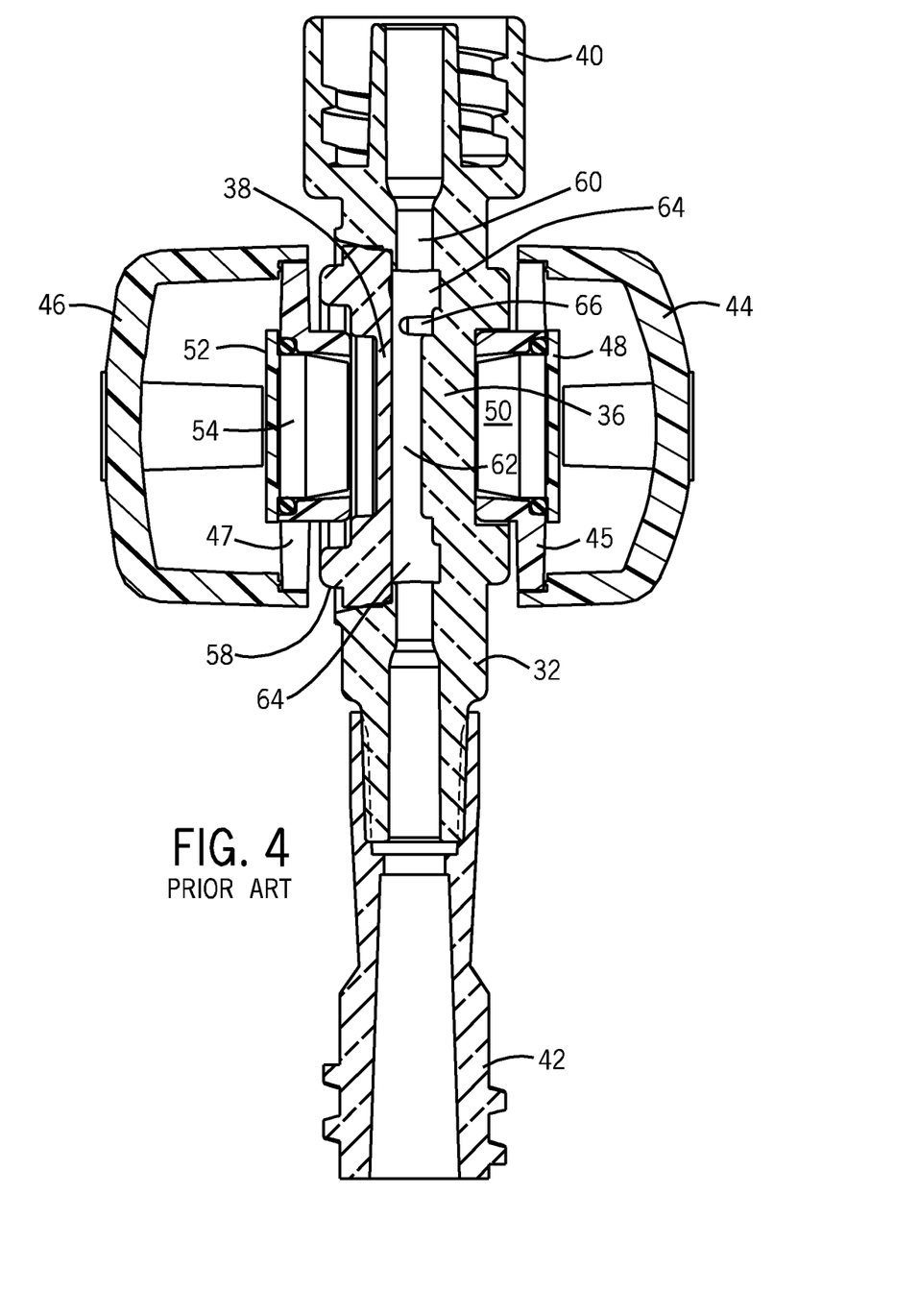
FIG. 4 is a cross-sectional view taken along line 4-4 in FIG. 2.

Referring now to FIGS. 2-4, the body of a prior art blood chamber 32 is made of molded, medical grade, clear polycarbonate. It includes two viewing windows 36, 38 (see FIG. 4). The inlet 40 and outlet 42 are designed to be compatible with standard medical industry connecting devices, conventionally known as luer lock connectors. In the blood chamber 32 shown in FIGS. 2-4, the inlet 40 is integrally molded with the blood chamber 32, whereas the outlet 42 consists of a suitable off-the-shelf connection adapter glued to the body of the blood chamber 32. The sensor assembly 34 includes an emitter subassembly 44 and a detector subassembly 46. As best shown in FIG. 4, an emitter circuit board 48 containing LEDs emitting light at substantially 660 nm, 810 nm and 1300 nm is mounted within the housing for the emitter subassembly 44. The photoemitters on the LED circuit board 48 emits visible and infrared light through a molded lens 50 that is mounted in the clip loop housing 45, and direct visible and infrared light through the viewing window 36 for the blood chamber 32. The controller 35 (FIG. 1), controls the operation of the respective LED emitters and detector(s) in order to multiplex the independent wavelength measurements so that the emitter and respective detector measurements remain correlated. Another circuit board 52 contains photodetectors, at least one made of silicon to detect light intensity at 810 nm and 660 nm, and at least one made of InGaAs to detect light intensity at 1300 nm. The detector circuit board 52 is mounted within the housing for the detector subassembly 46. A molded lens 54 is mounted in the clip loop housing 47 on the detector side of the clip covered by housing 46. The controller 35 includes data acquisition hardware and software which receives signals proportional to the intensities detected by the InGaAs and Si detector diodes. The viewing window 38 in the blood chamber 32 facilitates transmission of visible and infrared light at the respective wavelengths to the detectors on the circuit board 52 of the detector subassembly 46. Note that the viewing window 38 is molded into a separate insert 58 (referred to as the lens body 58) that is sonically welded to the body of the blood chamber 32. Blood flows from the inlet 40 through the passageway 60 to a central viewing region 62, also referred to herein as an internal blood flow cavity 62. The internal blood flow cavity provides a substantially flat, thin (e.g. less than 0.1 inches) viewing region for the blood flowing through the blood chamber 36. The multiplexed visible or infrared light at the three selected wavelengths, namely about 810 nm, 1300 nm and 660 nm, are transmitted through the blood flowing through the flat viewing region provided by internal blood flow cavity 62, as well as through the viewing windows 36, 38 in the chamber 32. A moat 64 surrounds the flat viewing region 62. The moat 64 is somewhat deeper than the flat viewing region 62. The moat 64 serves two primary purposes. First, the moat distributes non-laminar flow evenly and steadily through the viewing region. The moat 64 also provides a thicker region of blood which under most normal operating conditions optically isolates the detectors from detecting ducted or ambient light that does not pass through the direct path through the blood in the blood flow chamber. One or more turbulence posts 66 are located immediately upstream of the viewing region 62 to create steady eddy currents in the flow across the viewing region 62. While the flow through the viewing region 62 is non-laminar, the configuration of the blood chamber 32 shown in FIG. 4 results in steady flow through the viewing region 62 in terms of pressure and flow rate.

The housings 44 and 46 for the sensor clip assembly 34 include an inner housing frame 45, 47 which connects to the outer housing shells 44, 46. Each side of the inner housing frame 45, 47 provides an opening into which the molded lenses 50, 54 are mounted. The sensor assembly 34 is preferably a spring-loaded clip assembly adapted to be removably mounted to the blood chamber 32, as shown in FIG. 2. Both sides of the blood chamber 32 are molded such that the clip 34 will reside in a predetermined position when mounted to the blood chamber 32. As mentioned, blood chamber 32 is a single-use clear polycarbonate component. Between patient treatments, the blood chamber 32 is replaced along with the extracorporeal tubing 18, 24, and blood filter 22.

Figure 5:
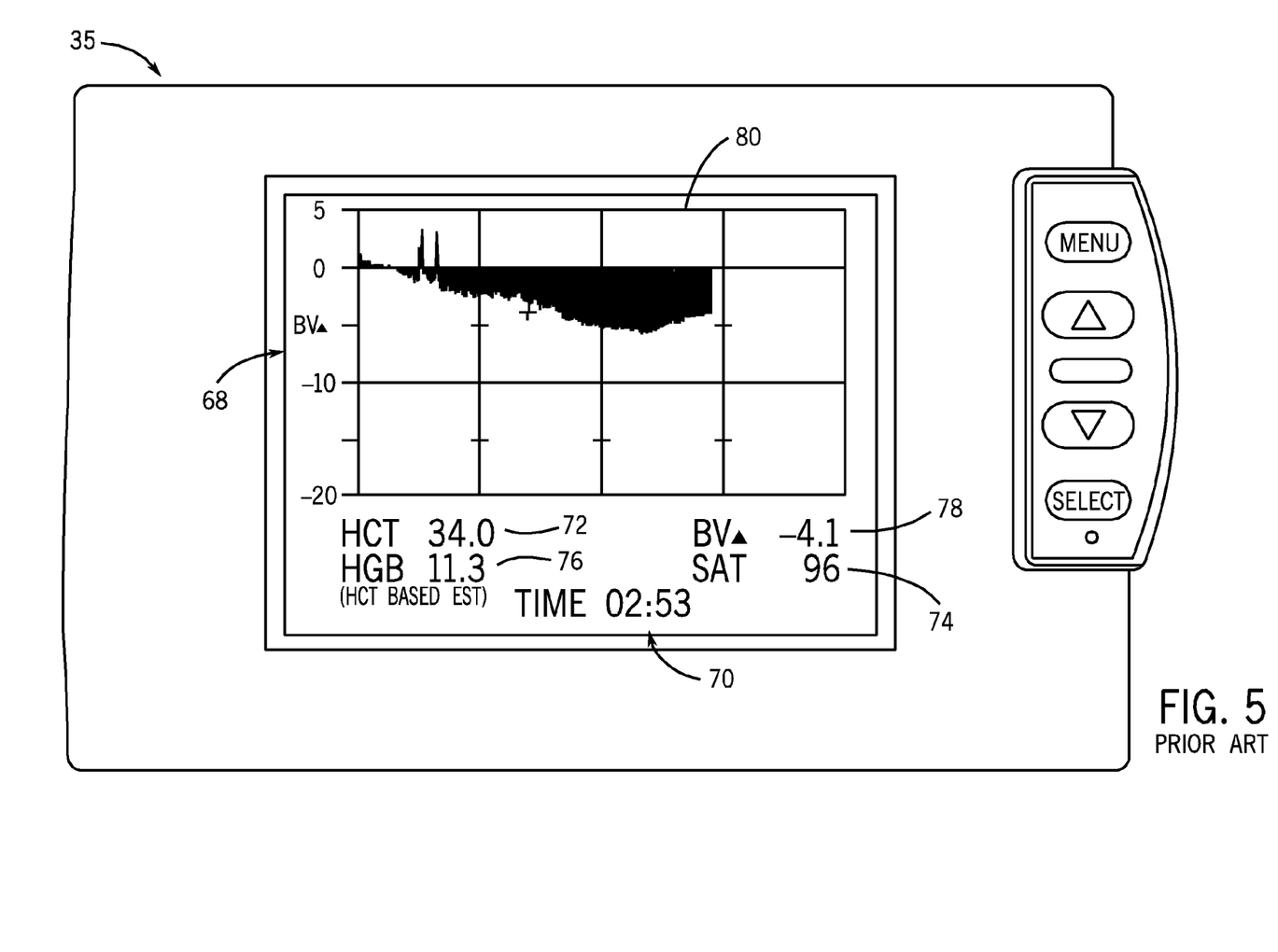
FIG. 5 is a front elevational view of a sample stand-alone host controller for the clip based optical blood monitor shown in FIG. 1.

FIG. 5 is a front elevational view of the stand-alone controller 35 for the prior art optical blood monitor 14. The controller 35 includes a display 68 that provides real-time blood monitoring data for the patient undergoing hemodialysis. The display in FIG. 5 illustrates the amount of time 70 that the patient 10 has been undergoing hemodialysis for the current treatment session. The time 70 displayed on the screen 68 in FIG. 5 is 2 hours and 53 minutes. The display 68 also illustrates real-time values for the optically monitored hematocrit (HCT) 72 and oxygen saturation (SAT) level 74, as well as the calculated values for hemoglobin (HGB) 76 and change in blood volume (BVΔ) during the treatment session 78. The graph 80 on the display 68 illustrates the change in the patient's blood volume over the course of the 2 hour and 53 minute treatment session. This data is displayed, as shown in FIG. 1, in a location that is located within the vicinity of the patient 10. The prior art CRIT-LINE® controller 35 also includes an RS-232 serial port which enables gathered data to be downloaded to commercially available patient data collection systems.

Periodically, the calibration and accuracy of the optical blood monitor 14 should be checked. In the art, this is normally done by placing the sensor clip 34 onto a verification filter (made of layered plastic having known optical qualities) that is mounted to the side of the controller 35. Calibration software within the controller 35 verifies the calibration of the unit, or allows the user to field calibrate the unit to bring it back to factory calibration settings. In some instances, it may be necessary to return the unit to the factory for calibration.

The intensity of the received light at each of the various wavelengths is reduced by attenuation and scattering from the fixed intensity of the visible and infrared light emitted from each of the LED emitters. Beers Law, for each wavelength of light, describes attenuation and scattering as follows:

$$i_n = I'_{o-n} * e^{-\epsilon_p X_p d_{pt}} * e^{-\epsilon_b X_b d_b} * e^{-\epsilon_p X_p d_{pr}} \quad \text{Eq. (3)}$$

where $i_n$=received light intensity at wavelength n after attenuation and scattering; $I_{o-n}$=transmitted light intensity at wavelength n incident to the measured medium; e=the natural exponential term; $\epsilon$=the extinction coefficient for the measured medium (p—polycarbonate, b—blood); X=the molar concentration of the measured medium (p—polycarbonate, b—blood); and d=the distance through the measured medium (pt—transmitting polycarbonate, b—blood, pr—receiving polycarbonate).

Since the properties of the polycarbonate blood chamber do not change, the first and third exponential terms in the above Eq. (3) are constants for each wavelength. Mathematically, then these constant terms are multiplicative with the initial constant term Io-n which represents the fixed intensity of the radiation transmitted from the respective LED emitter. For simplification purposes, Eq. (3) can be rewritten in the following form using bulk extinction coefficients and a modified initial constant I'on as follows:

$$i_n = I'_{o-n} * e^{-\alpha_b d_b} \quad \text{Eq. (4)}$$

where $i_n$=received light intensity at wavelength "n" after attenuation and scattering as though the detector were at the receive blood boundary; $\alpha$=the bulk extinction coefficient (p—polycarbonate, b—blood); $\alpha_b = \epsilon_b X_b$; $\alpha_p = \epsilon_p X_p$; and $I'_{o-n}$=the equivalent transmitted light intensity at wavelength n as if applied to the transmit blood boundary accounting for losses through the blood chamber. Note that the term $I'_{o-n}$ is the light intensity incident on the blood with the blood chamber losses included.

Using the approach defined in Eq. (4) above, the 810 nm wavelength which is isobestic for red blood cells and the 1300 nm wavelength which is isobestic for water can be used to determine the patient's hematocrit. The ratio of the normalized amplitudes of the measured intensity at these two wavelengths produces the ratio of the composite extinction values α for the red blood cells and the water constituents in the blood chamber, respectively. A mathematical function then defines the measured HCT value:

$$HCT = f\left[\frac{\ln\left(\frac{i_{810}}{I_{0-810}}\right)}{\ln\left(\frac{i_{1300}}{I_{0-1300}}\right)}\right] \quad \text{Eq. (4)}$$

where $i_{810}$ is the light intensity of the photo receiver at 810 nm, $i_{1300}$ is the infrared intensity of the photodetector at 1300 nm and $I_{0-810}$ and $I_{0-1300}$ are constants representing the intensity incident on the blood accounting for losses through the blood chamber. The above equation holds true assuming that the flow of blood through the blood chamber 32 is in steady state, i.e. steady pressure and steady flow rate.

The preferred function f[ ] is a second order polynomial having the following form:

$$HCT = f = A\left[\frac{\ln\left(\frac{i_{810}}{I_{0-810}}\right)}{\ln\left(\frac{i_{1300}}{I_{0-1300}}\right)}\right]^2 + B\left[\frac{\ln\left(\frac{i_{810}}{I_{0-810}}\right)}{\ln\left(\frac{i_{1300}}{I_{0-1300}}\right)}\right] + C. \quad \text{Eq. (6)}$$

A second order polynomial is normally adequate as long as the infrared radiation incident at the first and second wavelengths is substantially isobestic.

The oxygen saturation level, or the oxygenated hemoglobin level, is determined with a ratiometric model having the following form:

$$SAT = g\left[\frac{\ln\left(\frac{i_{660}}{I_{0-660}}\right)}{\ln\left(\frac{i_{810}}{I_{0-810}}\right)}\right] \quad \text{Eq. (7)}$$

where $i_{660}$ is the light intensity of the photo receiver at 660 nm, $i_{810}$ is the intensity of the photodetector at 810 nm and $I_{0-660}$ and $I_{0-810}$ are constants representing the intensity incident on the blood accounting for losses through the blood chamber. The function g[ ] is a mathematical function determined based on experimental data to yield the oxygen saturation level, again preferably a second order polynomial. It may be useful to use a pair of second order polynomials depending on the hematocrit value. Similar as in the case with the calculation for hematocrit, errors in the oxygen saturation value SAT can occur if there are errors in the measured intensity of the light at either the 660 nm or 810 nm wavelengths.

The microprocessor on the prior art controller implements several tasks. First, the microprocessor is responsible for operating the LED emitters and photodetectors and collecting data from the photodetectors. As the data signals are collected from the photodetectors, signal processing hardware and software filters the signals, and a microprocessor programmed with the ratiometric models explained above calculates the HCT and SAT levels in real time. The microprocessor also handles other calculations such as hemoglobin and change in blood volume and controls the display of this data on the screen display. In addition, as mentioned the prior art controller includes an RS-232 output data port, and the microprocessor controls the data output from this port as well. The main circuit board in the controller includes not only the microprocessor but also additional electronic hardware necessary for implementing accurate and reliable data collection, conversion and transmission.

Present Invention

Figure 6:
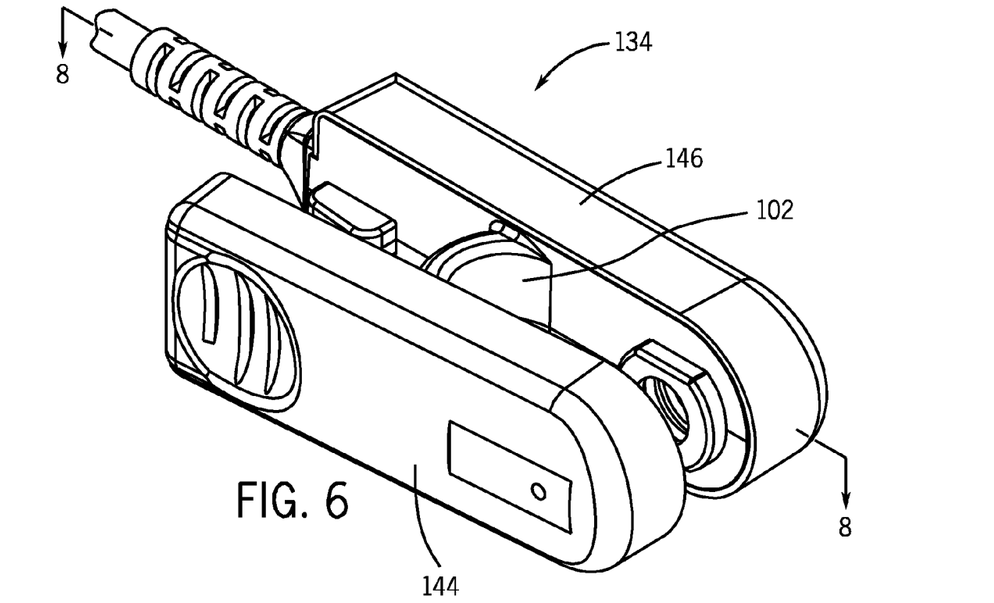
FIG. 6 is a perspective view showing a sensor clip assembly for an optical blood monitor constructed in accordance with the preferred embodiment of the invention.

FIG. 6 illustrates a sensor clip assembly 134 constructed in accordance with the preferred embodiment of the invention. The sensor clip assembly 134 includes an LED emitter arm 144 and a photodetector arm 146, which are connected via a spring biased bridge 102 as in the prior art. The LED emitter arm 144 contains preferably three LED emitters, one emitting infrared radiation at about 810 nm (e.g. 829 nm), another emitting infrared radiation at about 1300 nm and a third emitting red light at about 660 nm. The detector arm contains preferably two types of photodetectors: a silicon photodetector to detect the 660 and 810 nm wavelengths, and an indium gallium arsenide photodetector to detect the 1300 nm wavelength. As in the prior art, the LED emitter arm 144 and the photodetector arm 146 are welded or affixed into place over a blood chamber 32 (see FIG. 8) in order to monitor the hematocrit, hemoglobin, change in blood volume and oxygen saturation level of blood flowing through the blood chamber 32.

Figure 7:
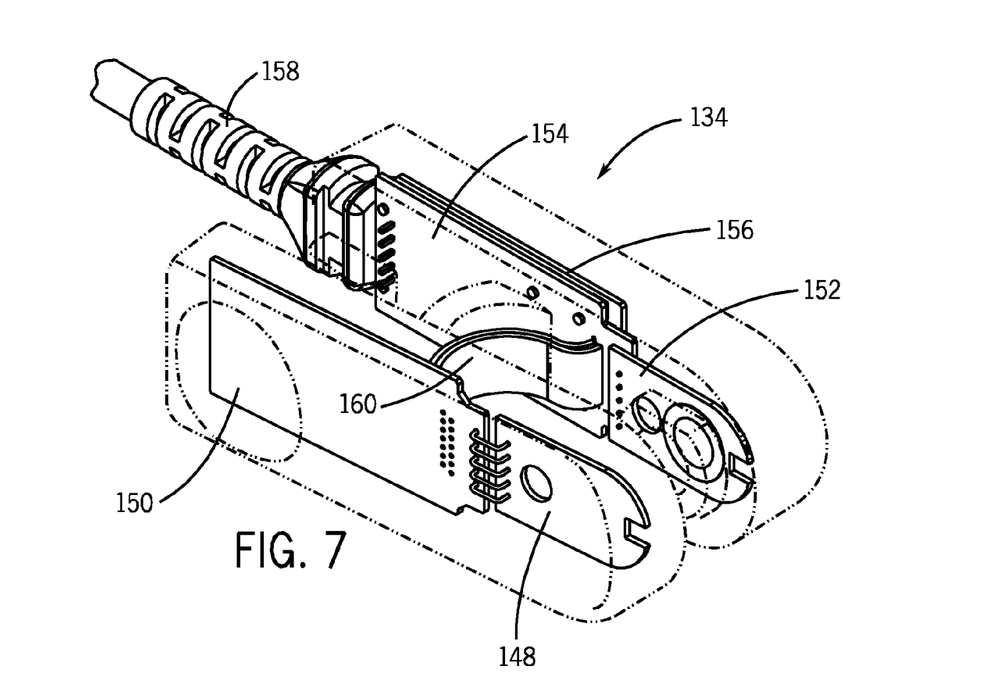
FIG. 7 is a view similar to FIG. 6 with the housings for the sensor clip assembly drawn in phantom in order to show internal components of the sensor clip assembly.

Referring to FIG. 7, the housings for the emitter arm 144 and the detector arm 146 have been removed to show internal components of the sensor clip assembly 134. The emitter arm of the sensor clip assembly 134 includes an LED circuit board 148 and a transmitter and processor circuit board 150. The detector arm of the sensor clip assembly 134 includes a detector circuit board 152, a receiver and communications board 154, and a power supply circuit board 156. A serial cable (e.g. USB) 158 is connected to the receiver and communications circuit board 154 and the power supply board 156 on the detector arm. A pair of seven conductor ribbon cables 160 is connected between the receiver and communications board 154 and the transmitter and processor board 150.

Figure 8:
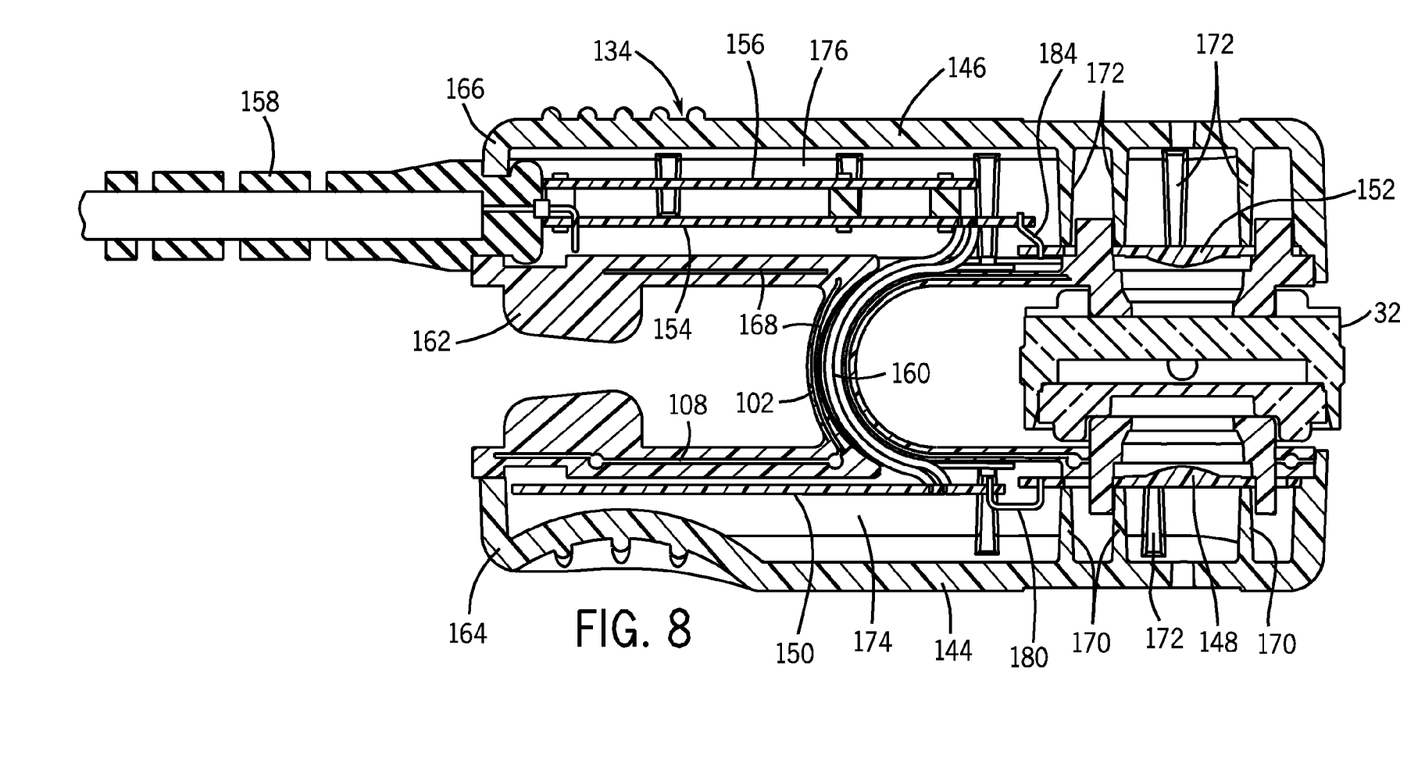
FIG. 8 is a cross-sectional view taken along line 8-8 in FIG. 6.

Referring to FIG. 8, the housing for the sensor clip assembly 134 includes an inner housing frame 162 as well as outer housing shells 164, 166 for the emitter arm 144 and 146 respectively. The inner housing frame 162 serves as the inner housing for both the emitter arm 144 and the detector arm 146. The bridge 102 spans between the portions of the inner frame housing corresponding to the emitter arm 144 and the detector arm 146. The bridge 102 includes an internal channel through which the pair of ribbon cables 160 passes. The inner housing frame 162 also includes a groove in each arm and across the bridge for a spring 168. The spring biases the distal ends of the emitter arm 144 and the detector arm 146 towards one another so that they clip securely over the blood chamber 32. The outer shell 164 for the emitter arm 144 includes stanchions 170 which secure the LED circuit board 148 in the proper position on the emitter arm 144. Similarly, the outer shell 166 for the detector arm 146 includes stanchions 172 which secure the detector circuit board 152 in the proper position.

The transmitter and processor circuit board 150 is contained within a compartment 174 in the emitter arm 144 defined by the inner housing frame 162 and the emitter arm shell 164. The receiver and communications circuit board 154 and the power supply board 156 are located in a compartment 176 defined by the inner housing frame 162 and the detector arm shell 166. In order to avoid vibration damage to the boards 150, 154 and 156 (e.g., due to sonic welding of the housing components), it has been found desirable that the board 150 in the compartment 174 and boards 154 and 156 in the compartment 176 not be mounted directly to the housing frame or outer shells. The power supply board 156 is physically mounted to the receiver and communications circuit board 154. One end of the receiver and communications circuit board 154 is supported by the flexible ribbon cables 160, and the other end is supported by the molded rubber strain relief for the serial cable (e.g. USB) 158. The receiver and communications board 154 is also connected via jumper 184 to the detector board 152. This mounting arrangement enables the boards 154 and 156 to float in the housing compartment 176 and isolate the boards from potentially damaging vibrations. Components on the detector board 152 as well as the LED board 148 are encapsulated within epoxy to secure the components to the boards 152, 142 and protect the components from vibration damage. The transmitter and processor circuit board 150 is held by the flexible ribbon cable 160 and also jumper 180. Similarly, this mounting arrangement enables the board 150 to float in the housing compartment 174 in the emitter arm 144 and isolate the board 150 from potentially damaging vibrations.

Figure 9:
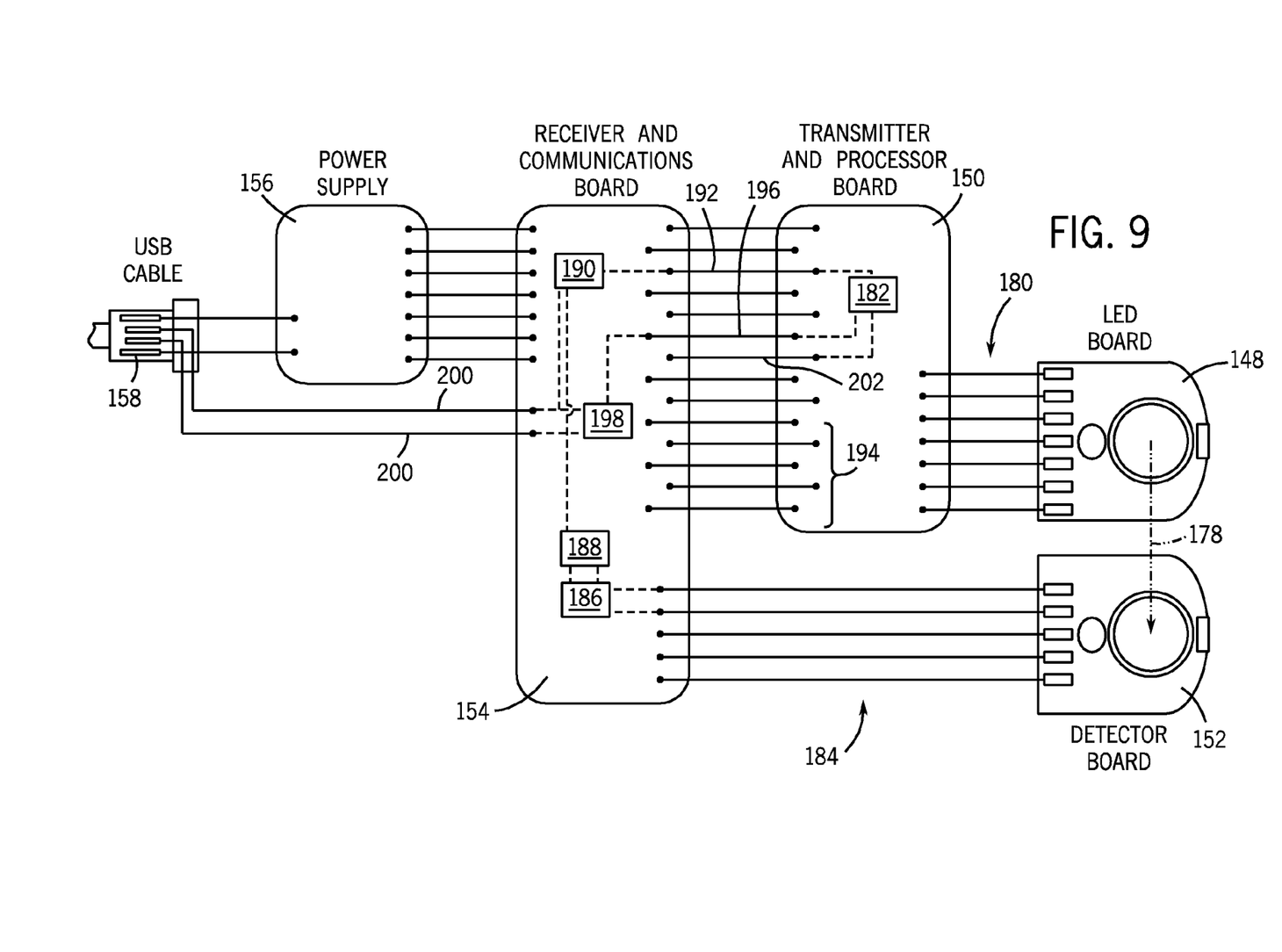
FIG. 9 is a schematic view illustrating the transmission and processing of data on the components in the sensor clip assembly illustrated in FIGS. 6 through 8.

FIG. 9 schematically depicts the communication of electrical signals in the sensor clip assembly 134. There are a plurality of electrical connections 180 between the transmitter and processor circuit board 150 and the LED circuit board 148. The transmitter and processor circuit board 150 includes a microprocessor 182, which among other tasks controls the output voltage to the LEDs on the LED board 148 via conductors 180. As mentioned, the LED circuit board preferably includes an LED emitting red light at 660 nm, an LED emitting infrared light at about 810 nm and another LED emitting infrared light at about 1300 nm. The microprocessor 182 preferably includes a built-in A-D convertor and a built-in D-A converter. The microprocessor 182 controls the current output to the LEDs, preferably so that each LED outputs a calibrated known intensity at the respective wavelength. The microprocessor 182 needs to be calibrated to account for differences in output efficiency of the LEDs for each clip assembly. The scope of this invention is not directed to the method of calibration, although it is noted that it may be desirable to recheck the calibration from time to time as the clip assembly unit is in the field. If desirable, a field calibration system may be implemented as with the prior art systems. Alternatively, since the sensor clip assembly is relatively inexpensive to manufacture, it may be desirable to require that the sensor clip assembly be replaced once the clip assembly falls out of calibration.

Still referring to FIG. 9, dashed line 178 depicts visible or infrared light being transmitted from an LED on the LED circuit board 148 to one of the photodetectors on the detector circuit board 152. The detector board 152 as mentioned includes at least one silicon photodetector and at least one indium gallium arsenide photodetector. The microprocessor 182 implements a multiplexing routine so that LED emission is active and correlated to its respective received signal through the photo diodes for visible and infrared light. One example of multiplexing is the time based switching of each LED and matching detector for unique successive time periods resulting in time period measurements unique to each wavelength. This time based method is called commutation. A plurality of conductors connects the detector board 152 to the receiver and communications circuit board 154. The conductors 184 include paths to ground, as well as electrical connections to the anode and cathode of the silicon diode photodetector(s) and an electrical connection to the anode and cathode of the indium gallium arsenide diode photodetector(s). The signals (µA) from the photodetectors are normally relatively weak with a poor signal to noise ratio. The receiver and communications board includes transimpedance amplifiers 186 that convert the current signals (µA) from the silicon and indium gallium arsenide photodetectors into analog voltage signals (mV). The analog voltage signals from the transimpedance amplifier 186 are transmitted to digital trim pots 188. Conductors 194 transmit timing signals from the microprocessor 182 to control the synchronization of the trim pots 188 in order to ensure that proper time-based commutation occurs. The time-commutated, voltages signals from the trim pots 188 are transmitted to a summing junction. The composite time-commutated, voltage signal from the summing junction is then processed through signal filtering hardware 190 to strip noise from the analog voltage signal. The cleaned analog signal is then separated by the microprocessor 182 through line 192 to a built-in A-D converter where and each signal is measured separately. These de-commutated signals represent the intensity of the visible and infrared light at the respective wavelength 660 nm, 810 nm, or 1300 nm as appropriate as depending on the time in the de-commutation process. The microprocessor 182 is programmed with the calibrated, ratiometric model to calculate the patient's hematocrit. It is also preferably programmed with a calibrated, ratiometric model to calculate the patient's oxygen saturation level. The HCT and SAT values are based on the detected signals from the silicon and indium gallium arsenide detectors that are filtered, de-commutated and calculated by the microprocessor 182. The ratiometric model for calculating the HCT is of the form of Eq. (5) referred to above, and is preferably a second order polynomial having a form as described in the above Eq. (6). The ratiometric model for determining the oxygen saturation level (SAT) is of the form of Eq. (7) above, and preferably is in the form of a second order polynomial as well.

The calculated values for HCT and SAT are outputted as digital signals by the microprocessor 182 via conductor 196 and are transmitted to a serial communications chip 198 on the receiver and communications board 154. The serial communications chip converts the digital signals from the microprocessor 182 into data signals that are transmitted via lines 200 to the serial cable 158. It is preferred to transmit the data signals by a USB cable implementing differential data signaling techniques, i.e. redundant digital signals 180° out of phase, in order to facilitate common mode rejection as is known in the art. The data transmitted via the serial (e.g. USB) cable preferably includes systems status information as well as the real-time HCT and SAT information, and also preferably real-time hemoglobin and change in volume information that can be calculated from the HCT information. Other data calculated by the microprocessor can also be transmitted via the serial (e.g. USB) cable in a similar manner. Desirably, a USB cable transmits the data to another piece of equipment that can accept the USB cable receptacle and data as is known in the art. If desired, instructions to the sensor clip assembly 134 can be transmitted from the equipment over the USB cable, through the USB communications chip 198 on the receiver and communications board and via conductor 202 to control the microprocessor 182 as well.

When a USB cable at 158 is used, the cable also provides 5V USB power to the power supply board 156. The power supply board 156 conditions the power from the USB port, and isolates the electrical components on the sensor clip assembly from direct connection to the USB power which may not be smooth enough for reliable operation of the sensor clip assembly. The power supply board regenerates quiet and precise 5V and 3.3V power in order to facilitate reliable operation of the LED emitter and detector pairs as well as the other electronic components on the sensor clip assembly. The power supply board uses switching regulators to convert between the 5V and the 3.3V power signals as needed. It has been found that the switching regulators are quite efficient and do not generate a significant heat load.

As mentioned, one of the advantages of the invention is that weak signal data from the detector board 152 is collected and converted into digital signals without significant transmission losses because of the close proximity of the detector board 152 to the receiver and communications board 154. Converting the data into digital form at the receiving point, as mentioned, allows the system to drive the LED emitters with lower electrical currents and yet maintain suitable signal to noise ratios. The use of lower LED drive currents lowers heat generation and also tends to extend the useful calibrated life of the LEDs.

The invention is therefore quite useful even in applications where it is desired to place a display unit at or near a conventional hemodialysis system. Such a separate display unit may for example comprise a personal computer programmed with software to display the patient's HCT, SAT, hemoglobin and change in blood volume data in real time. On the other hand, such display unit may include merely a display, a user interface, and a simplified circuit board and microprocessor that is able to display the data on the screen as in the prior art, and also provide data to other pieces of equipment via a serial port (e.g. RS-232, host USB, etc.). The microprocessor on such a display unit need not have the capability of implementing the ratiometric models, or be subject to calibration requirements.

A sensor clip assembly 134 constructed in accordance with the invention can be used in connection with other equipment as well, as long as the equipment includes the capability of accepting data via a matching serial connection (e.g. USB). Of course, the invention should not be limited to the use of only a USB cable. Other transmission cables can be used in accordance with the broad aspects of the invention.

The described use and embodiment of the invention is to be considered in all respects as only illustrative and not restrictive.

What is claimed is:

1. A sensor clip assembly for an optical monitoring system having a blood chamber with a viewing area for optically monitoring extracorporeal blood flow through the blood chamber, the sensor clip assembly comprising:
   an emitter arm, comprising at least two light-emitting diode (LED) emitters;
   a detector arm, comprising a silicon photodetector and an indium gallium arsenide photodetector, wherein the at least two LED emitters of the emitter arm and the photodetectors of the detector arm are disposed such that, with the sensor clip assembly attached to the blood chamber, the photodetectors are configured to detect light transmitted from the LED emitters that has passed through extracorporeal blood in the blood chamber under steady-state conditions of substantially steady pressure and substantially steady flow rate;
   a processor, programmed with a ratiometric model, configured to determine a hematocrit (HCT) level corresponding to the steady-state extracorporeal blood in the blood chamber based on light intensity of the light transmitted through the extracorporeal blood and detected by the photodetectors; and
   an output port, configured to provide an output data signal corresponding to the determined HCT level to an external computing device connected to the sensor clip assembly;
   wherein the sensor clip assembly is pre-calibrated independent of the external computing device to which the sensor clip assembly is configured to be connected.

2. The sensor clip assembly as recited in claim 1, further comprising a power supply circuit board comprising a power supply circuit for regulating currents to be supplied to the at least two LED emitters.

3. The sensor clip assembly as recited in claim 1, wherein the processor is configured to output a digital signal corresponding to the determined HCT level at a programmable sampling rate.

4. The sensor clip assembly as recited in claim 1, wherein the output port is a Universal Serial Bus (USB) port.

5. The sensor clip assembly as recited in claim 1, wherein the sensor clip assembly further comprises a flexible conductor ribbon cable connecting at least one circuit board disposed within the emitter arm with at least one circuit board disposed within the detector arm.

6. The sensor clip assembly as recited in claim 1, further comprising:
   a structural bridge between the emitter arm and the detector arm; and
   a spring, biasing the emitter arm and the detector arm to close towards one another so as to facilitate attachment of the sensor clip assembly to the blood chamber.

7. The sensor clip assembly recited in claim 1, wherein a first LED emitter of the at least two LED emitters is configured to emit light at a first wavelength and a second LED emitter of the at least two LED emitters is configured to emit light at a second wavelength; and
   wherein processor is configured to apply the following formula to determine the HCT level corresponding to the extracorporeal blood in the blood chamber:

$$HCT = f\left[\frac{\ln\left(\frac{i_{\lambda 2}}{I_{0-\lambda 2}}\right)}{\ln\left(\frac{i_{\lambda 1}}{I_{0-\lambda 1}}\right)}\right]$$

where $i_{\lambda 1}$ is the detected light intensity at the first wavelength;

$i_{\lambda 2}$ is the detected light intensity at the second wavelength;

$I_{o-\lambda 1}$ is a calibration constant for the incident light intensity illuminating the blood taking into account loss light intensity of the first wavelength due to path losses in the emitter and detector arms, including losses from air gaps and lenses, and losses from the body of the blood chamber;

$I_{o-\lambda 2}$ is a calibration constant for the incident light intensity illuminating the blood taking into account loss of light intensity of the second wavelength due to path losses in the emitter and detector arms, including losses from air gaps and lenses, and losses from the body of the blood chamber; and $f$ is a function that fits log ratio mathematics to yield HCT.

8. The sensor clip assembly as recited in claim 7, wherein the first wavelength is substantially isobestic for water and the second wavelength is substantially isobestic for hemoglobin.

9. The sensor clip assembly as recited in claim 7, wherein the function $f$ is a second order polynomial defined by the following equation:

$$HCT = f\left[\frac{\ln\left(\frac{i_{\lambda 2}}{I_{0-\lambda 2}}\right)}{\ln\left(\frac{i_{\lambda 1}}{I_{0-\lambda 1}}\right)}\right] = A\left[\frac{\ln\left(\frac{i_{\lambda 2}}{I_{0-\lambda 2}}\right)}{\ln\left(\frac{i_{\lambda 1}}{I_{0-\lambda 1}}\right)}\right]^2 + B\left[\frac{\ln\left(\frac{i_{\lambda 2}}{I_{0-\lambda 2}}\right)}{\ln\left(\frac{i_{\lambda 1}}{I_{0-\lambda 1}}\right)}\right] + C.$$

10. The sensor clip assembly recited in claim 7, wherein the emitter arm further comprises a third LED emitter for emitting light at a third wavelength.

11. The sensor clip assembly recited in claim 10, wherein the processor is further configured to determine an oxygen saturation level (SAT) corresponding to the extracorporeal blood in the blood chamber based on light signals detected by the at least one photodetector; and
wherein the processor is configured to apply the following formula:

$$SAT = g\left[\frac{\ln\left(\frac{i_{\lambda 3}}{I_{0-\lambda 3}}\right)}{\ln\left(\frac{i_{\lambda 1}}{I_{0-\lambda 1}}\right)}\right]$$

where: $i_{\lambda 2}$ is the detected light intensity at the second wavelength;
$i_{\lambda 3}$ is the detected light intensity at the third wavelength;
$I_{o-\lambda 2}$ is a calibration constant for the incident light intensity illuminating the blood taking into account loss of light intensity of the second wavelength due to path losses in the emitter and detector arms, including losses from air gaps and lenses, and losses from the body of the blood chamber; $I_{o-\lambda 3}$ is a calibration constant for the incident light intensity illuminating the blood taking into account loss of light intensity of the third wavelength due to path losses in the emitter and detector arms, including losses from air gaps and lenses, and losses from the body of the blood chamber; and
g is a function that fits log ratio mathematics to yield SAT.

12. The sensor clip assembly recited in claim 11, wherein the third wavelength is sensitive to signal changes due to oxygenation of hemoglobin.

13. The sensor clip assembly recited in claim 11, wherein the function g is a second order polynomial defined by the following equation:

$$SAT = g\left[\frac{\ln\left(\frac{i_{\lambda 3}}{I_{0-\lambda 3}}\right)}{\ln\left(\frac{i_{\lambda 2}}{I_{0-\lambda 2}}\right)}\right] = A\left[\frac{\ln\left(\frac{i_{\lambda 3}}{I_{0-\lambda 3}}\right)}{\ln\left(\frac{i_{\lambda 2}}{I_{0-\lambda 2}}\right)}\right]^2 + B\left[\frac{\ln\left(\frac{i_{\lambda 3}}{I_{0-\lambda 3}}\right)}{\ln\left(\frac{i_{\lambda 2}}{I_{0-\lambda 2}}\right)}\right] + C.$$

14. The sensor clip assembly recited in claim 1, wherein the processor is disposed on a circuit board, and wherein the sensor clip assembly further comprises:
an emitter housing;
wherein the circuit board is mounted within the emitter housing without directly contacting the emitter housing so as to isolate the circuit board from vibration.

15. The sensor clip assembly recited in claim 14, wherein the circuit board is mounted within the emitter housing using a ribbon cable and a jumper.

16. The sensor clip assembly recited in claim 1, further comprising:
a detector housing;
a power supply board; and
a receiver and communications board;
wherein the power supply board and the receiver and communications board are mounted within the detector housing without directly contacting the detector housing so as to isolate the power supply board and the receiver and communications board from vibration.

17. The sensor clip assembly recited in claim 16, wherein the power supply board and the receiver and communications board are mounted within the detector housing using a strain relief for a serial cable, a ribbon cable and a jumper.

18. The sensor clip assembly recited in claim 1, wherein the photodetectors are each configured to output an analog current signal corresponding to the detected light intensity;
wherein the sensor clip assembly further comprises:
a transimpedance amplifer for converting the analog current signal to an analog voltage signal;
signal filtering hardware for filtering noise from the analog voltage signal; and
an analog-to-digital converter for converting the filtered analog voltage signal to a digital signal corresponding to the detected light intensity, wherein the processor is configured to utilize the digital signal in determining the hematocrit level.

\* \* \* \* \*